United States Patent [19]

Hallström

[11] 4,374,087

[45] Feb. 15, 1983

[54] METHOD OF STERILIZING MATTRESSES, LAUNDRY SACKS AND SIMILAR ARTICLES IN A STERILIZING APPARATUS

[76] Inventor: Bengt O. Hallström, S-182 65, Djursholm, Sweden

[21] Appl. No.: 274,459

[22] Filed: Jun. 17, 1981

[51] Int. Cl.³ .............................................. A61L 9/00
[52] U.S. Cl. ..................................... 422/34; 422/105; 422/297; 422/306; 422/311
[58] Field of Search ................ 422/34, 295, 297, 105, 422/300, 306, 311

[56] References Cited

U.S. PATENT DOCUMENTS

| | | | |
|---|---|---|---|
| 337,522 | 3/1886 | Schimmel | 422/297 |
| 2,007,738 | 7/1935 | Baer | 422/34 |
| 2,069,036 | 1/1937 | Howard | 422/295 |
| 3,897,210 | 7/1975 | Gruber et al. | 422/34 |

FOREIGN PATENT DOCUMENTS

| | | | |
|---|---|---|---|
| 236071 | 10/1961 | Canada | 422/34 |
| 539119 | 11/1931 | Fed. Rep. of Germany | 422/295 |
| 2708068 | 9/1978 | Fed. Rep. of Germany | 422/28 |

Primary Examiner—Bernard Norzick

[57] ABSTRACT

A method of sterilizing mattresses, laundry sacks and similar articles in a sterilizing apparatus comprising a sterilization chamber with a surface to carry said articles, and a circulation system which, besides said sterilization chamber includes a fan, a pressure pipe from the fan to the sterilization chamber and a suction pipe from the sterilization chamber to the fan. The sterilization is carried out in a work cycle comprising a combination of a gas-filling phase, a sterilizing phase, at least one gas-emptying phase, at least one ventilation phase and a final phase, the sterilization gas being removed from the circulation system during the gas-emptying phase by means of a water suction means and thus being mixed with water, while at the same time filtered air is added to the circulation system.

4 Claims, 1 Drawing Figure

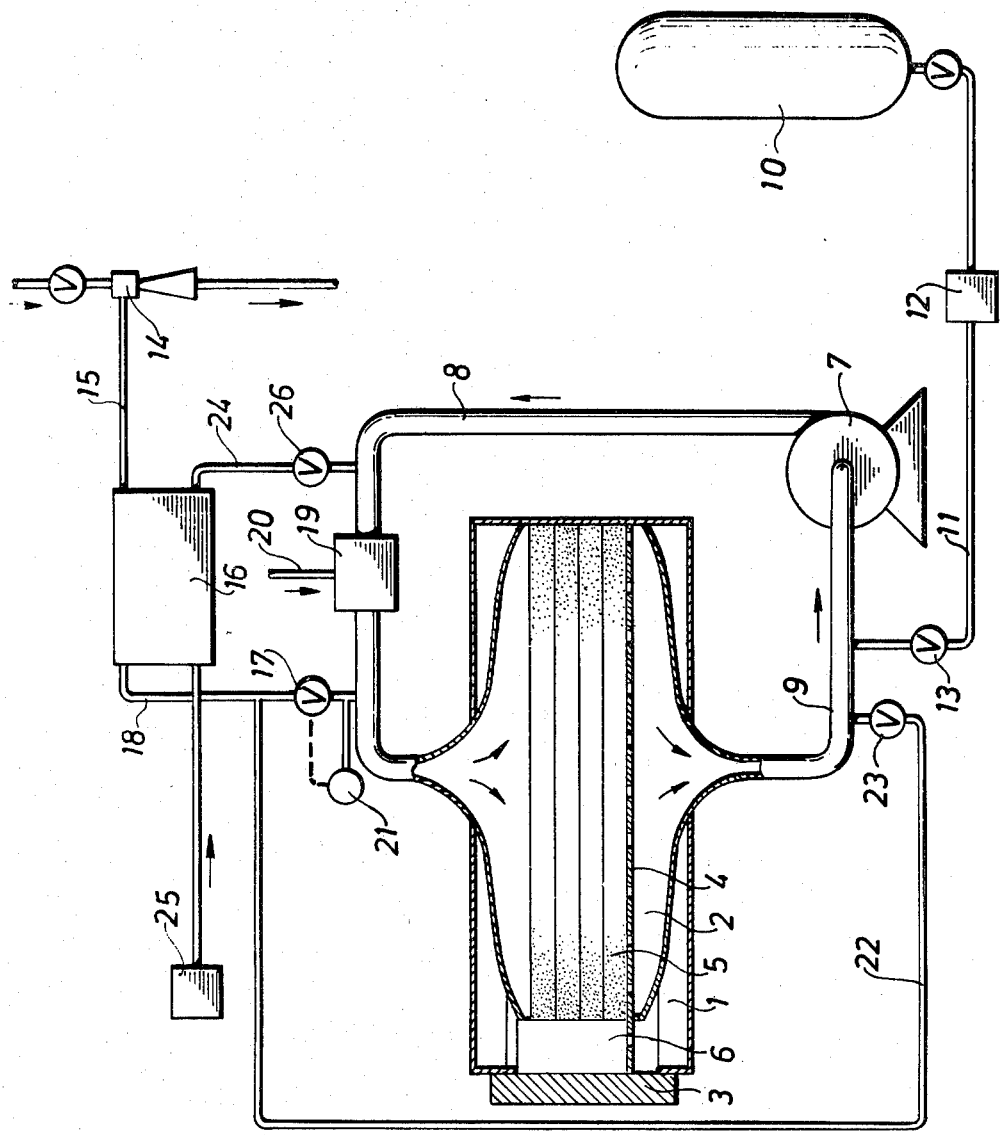

METHOD OF STERILIZING MATTRESSES, LAUNDRY SACKS AND SIMILAR ARTICLES IN A STERILIZING APPARATUS

The present invention relates to a method of sterilizing mattresses, laundry sacks and similar articles in a sterilizing apparatus. The invention also relates to an apparatus for performing said method, comprising a sterilization chamber with a support to carry said articles, a circulation system which, besides said sterilization chamber includes a fan, a pressure pipe from the fan to the sterilization chamber and a suction pipe from the sterilization chamber to the fan. The apparatus also includes a gas source which is connected by a gas-supply pipe to said suction pipe, and an evacuation pipe for removing gas from the circulation system.

The purpose of the invention is to achieve an improved method and an improved sterilization apparatus for sterilizing mattresses, laundry sacks and similar articles in a satisfactory and efficient manner with an apparatus requiring no special ventilation installation.

This and other objects are achieved according to the present invention in that the method comprises a gas-filling phase, a sterilizing phase, at least one gas-emptying phase, at least one ventilation phase and a final phase, and that the sterilization gas is removed from the circulation system during the gas-emptying phase by means of a water suction means and is thereby mixed with water, and that filtered air is simultaneously supplied to the circulation system.

The invention is further described in the following with reference to a preferred embodiment of a sterilization apparatus illustrated in the drawing.

The shown sterilization apparatus comprises a casing 1 defining a sterilizing chamber 2 which is closable by a cover 3. A grid 4 of steel wire is provided in the sterilizing chamber 2 to carry the object or objects 5 to be treated. A suitable sealing means 6 is arranged in contact with the objects 5 leaving no gap, so that the sterilizing gas is forced through the objects, i.e. there being no free passage beside them. In the case shown the objects consists of a number of mattresses placed one on top of the other but other objects such as laundry sacks and so on can of course be treated.

A fan 7 is connected via a pressure pipe 8 to the top of the sterilizing chamber and via a suction pipe 9 to the bottom of the sterilizing chamber. Gas from a gas cylinder 10 is fed into the suction pipe 9 via a gas-supply pipe 11 containing a measuring and control means 12 and a valve 13 regulated by said measuring and control means 12.

A water suction means 14 is connected to the pressure pipe 8 by means of a pipe 15 passing through a heat-exchanger 16 and a pipe 18 provided with a valve 17. A gas-heating means 19 is provided to heat the gas. This is thermostatically controlled and mounted in the pressure pipe 8 before the pipe 18 from the water suction means 14, a pipe 20 supplying water being connected to the gas-heating means.

A pressure-regulating safety device 21 is also arranged in the pipe 18 between valve 17 and pressure pipe 8 in order to open valve 17 and start the water suction when the pressure exceeds a predetermined value.

An emptying pipe 22 is connected between the suction pipe 9 and the pipe 18 between valve 17 and water suction means 14. This emptying pipe 22 contains a valve 23. An air-supply pipe 24 is also connected to the pressure pipe 8 between the fan 7 and the gas-heating means 19, said air supply pipe 24 passing through the heat-exchanger 16 and containing an air filter 25 and a valve 26.

The work cycle of the sterilizing apparatus described above comprises the following phases: gas-filling phase, sterilizing phase, gas-emptying phase, ventilation phase and final phase.

Mattresses or other objects are first placed in the sterilizing chamber 2 and the sealing means 6 is arranged so that there is no gap which might lead the sterilizing gas past the mattresses. The cover 3 is then closed and the sterilizing program regulating the various phases and their courses is switched on.

Gas-filling Phase

The sterilizing apparatus is filled with gas from the gas cylinder 10 since the valve 13 is opened and the air, which is lighter than the sterilization gas, is drawn out through pipes 18 and 15 since valve 17 is opened and the water suction means 14 started. When the determined quantity of gas has been supplied with the help of the measuring and control means 12, valve 13 in gas supply pipe 11 and valve 17 in pipe 18 and the water suction means 14 are turned off.

Sterilizing Phase

The sterilizing phase is introduced by the fan 7 being started and the gas thus circulating is heated by the thermostatically controlled gas-heating means 19. When the gas has reached sterilizing temperature a certain amount of water is vaporized, about 50 ml, by being supplied drop by drop to the gas-heating means via the water supply pipe 20. To prevent over-pressure arising in the sterilizing apparatus when the gas is heated and the water vaporized, the pressure-regulating safety means 21 is connected, which opens valve 17 and starts the water suction means 14 when the pressure exceeds a predetermined value.

When the gas has reached the correct temperature and humidity, fan 7 is turned off. This is only switched on a few times during the continuation of the sterilizing phase and operates for about 30 seconds in order to circulate the sterilizing gas through the mattresses.

Gas-emptying Phase

When the sterilizing phase is finished after a predetermined time, valve 26 in the air supply pipe 24 and valve 23 in the emptying pipe 22 are opened at the same time as the water suction means 14 is started. The sterilizing gas is thus removed from the system through pipes 18 and 15 and clean, filtered air flows in through air supply pipe 24. In order to achieve better economy, the hot sterilizing gas leaving and the cold air entering are subjected to heat-exchange in heat-exchanger 16.

Ventilation Phase

When the sterilizing gas has been removed from the system, valves 26 and 23 are closed and fan 7 is started so that the circulating air is heated during its passage through the gas-heating means 19. The fan 7 is on throughout the ventilation phase.

When the fresh air is considered to contain too much sterilizing gas, it is withdrawn and more air is supplied. The complete gas-emptying and ventilation phases are thus repeated.

The number of ventilation phases and their duration may vary and can be determined empirically.

Final Phase

When the ventilation phase(s) is/are finished valves 26 and 23 are opened and at the same time the water suction means 14 is started so that clean air will be drawn into the apparatus. The articles are now ready to be taken out for use.

According to a preferred embodiment of the invention a sterilizing gas is used which contains ethylene oxide, for instance a gas containing 90% carbon dioxide and 10% ethylene oxide, so that the ethylene oxide reacts with the water in the water suction means during the emptying phase to form ethylene glycol which is removed with the drainage water. This means that the sterilizing apparatus need not be provided with any special ventilation installation.

The sterilizing apparatus can with advantage sterilize up to four mattresses simultaneously. Laundry sacks can also be sterilized if a special sealing means is used.

The temperature during the sterilizing phase is within the interval of from 50° to 60° C., the relative humidity is about 0.5 and the pressure about 1 ata.

The ethylene oxide which is absorbed by the mattresses during the sterilizing phase is desorbed by hot air being caused to flow through the mattresses.

What I claim is:

1. A method of sterilizing mattresses, laundry sacks and similar articles comprising:
(a) placing and sealing said articles in a sterilizing chamber of a sterilizing apparatus, said sealing being effected so as to leave no gap beside or between said articles;
(b) removing the air in said chamber and replacing the air with a sterilization gas;
(c) circulating said gas through the sterilizing chamber while heating and humidifying said gas;
(d) removing said gas from said chamber and replacing said gas with clean, filtered air which is heated during the period of its circulation through the sterilizing chamber; and
(e) drawing clean air into said chamber and discharging of the sterilized articles.

2. A method according to claim 1, wherein a water suction means is used in steps (b), (d) and (e).

3. A method according to claim 1 wherein the sterilization is performed with a sterilization gas containing ethylene oxide.

4. An apparatus for sterilizing mattresses, laundry sacks and similar articles, comprising a sterilization chamber with a surface to carry said articles, a sealing means effective for leaving no gaps beside or between said articles, and a circulation system which, besides said sterilization chamber includes a fan, a pressure pipe from the fan to the sterilization chamber and a suction pipe from the sterilization chamber to the fan; a sterilization gas source which is connected by a gas-supply pipe to said suction pipe, and an evacuation pipe for removing gas from the circulation system, said evacuation pipe being connected to a water suction means arranged to draw off the sterilization gas and mix this with water, and an air supply pipe provided with an air filter being connected to the circulation system.

* * * * *